US010595956B2

(12) United States Patent
Naslund

(10) Patent No.: US 10,595,956 B2
(45) Date of Patent: Mar. 24, 2020

(54) MARKER LOADING ASSEMBLY

(71) Applicant: Camtomsam AB, Huddinge (SE)

(72) Inventor: Ingemar Naslund, Huddinge (SE)

(73) Assignee: Camtomsam AB, Huddinge (SE)

( * ) Notice: Subject to any disclaimer, the term of this patent is extended or adjusted under 35 U.S.C. 154(b) by 805 days.

(21) Appl. No.: 14/951,553

(22) Filed: Nov. 25, 2015

(65) Prior Publication Data

US 2017/0143444 A1    May 25, 2017

(51) Int. Cl.
*A61B 90/00* (2016.01)
*A61B 17/00* (2006.01)

(52) U.S. Cl.
CPC .... *A61B 90/39* (2016.02); *A61B 2017/00849* (2013.01); *A61B 2090/3954* (2016.02); *A61B 2090/3987* (2016.02)

(58) Field of Classification Search
None
See application file for complete search history.

(56) References Cited

U.S. PATENT DOCUMENTS

| | | | | |
|---|---|---|---|---|
| 4,543,091 | A * | 9/1985 | Froning | A61B 6/12 248/297.51 |
| 7,118,523 | B2 * | 10/2006 | Loffler | A61N 5/1027 600/3 |

(Continued)

FOREIGN PATENT DOCUMENTS

WO    2012/154116    11/2012

*Primary Examiner* — Katherine L Fernandez

(74) *Attorney, Agent, or Firm* — Renner, Otto, Boisselle & Sklar, LLP

(57) ABSTRACT

A marker loading assembly for transferring an elongated positioning marker from a loader needle of said assembly into an insertion needle of a medical insertion device, the marker loading assembly comprises an elongated hollow housing having a manoeuvring end and a marker transfer end, and a loader needle mounted within said loading assembly along a longitudinal axis of said assembly, said loader needle being adapted to receive and hold said positioning marker until the positioning marker is transferred to said insertion needle, a transfer opening provided at the marker transfer end and being adapted to receive a distal end of the insertion needle, said transfer opening being provided with a shape gradually opening up in a direction away from said manoeuvring end, and said transfer opening at its narrow end leading to a transfer channel arranged along said longitudinal axis, and wherein the transfer channel has a circular cross-sectional shape having a diameter slightly larger than an outer diameter of the insertion needle or of an outer protective sleeve provided on the outside of the insertion needle, and wherein a loading end of the loader needle is concentrically arranged in the transfer channel such that an annular space having a predetermined length along the longitudinal axis is provided around the loading end, and wherein the outer diameter of the loader needle is slightly smaller than the inner diameter of the insertion needle, which enables the distal end of the insertion needle to be inserted into said annular space in the transfer channel and simultaneously the loading end of the loader needle to be inserted into the distal end of the insertion needle to set said assembly in a marker loading ready state, and wherein the loading assembly further comprises a transfer mandrel, said transfer mandrel being adapted to be arranged within said loading needle and being arranged to receive a force in the direction towards the insertion needle and thereby achieve transfer of the marker from the loader needle into the distal end of the insertion needle.

13 Claims, 2 Drawing Sheets

(56) References Cited

U.S. PATENT DOCUMENTS

| | | | |
|---|---|---|---|
| 9,669,113 B1* | 6/2017 | Sirimanne | A61K 49/006 |
| 2001/0008950 A1* | 7/2001 | Vitali | A61N 5/1007 |
| | | | 600/7 |
| 2003/0088144 A1* | 5/2003 | Terwilliger | A61N 5/1007 |
| | | | 600/8 |
| 2010/0261946 A1* | 10/2010 | Kaplan | A61K 41/0038 |
| | | | 600/8 |
| 2013/0006286 A1* | 1/2013 | Lavelle | A61B 17/3468 |
| | | | 606/185 |
| 2013/0046174 A1* | 2/2013 | Fischell | A61B 90/39 |
| | | | 600/431 |
| 2014/0088419 A1 | 3/2014 | Näslund | |

\* cited by examiner

MARKER LOADING ASSEMBLY

TECHNICAL FIELD

The present disclosure relates to a marker loading assembly for transferring an elongated positioning marker from a loader needle of the assembly into an nsertion needle of a medical insertion device, easily without the risk of needle-stick injuries.

BACKGROUND

In WO-2012/154116 (corresponding to US-2014/0088419) from the same applicant as the present application and incorporated as reference in its entirety herein, is a positioning marker known intended to be inserted into tissue, and which is applicable in relation to the marker loading assembly as disclosed in the present application.

When treating cancer tumours the physician is preparing the treatment e.g. by planning how large the dose of the medicine shall be or how much the radiation therapy shall comprise. Basis for the planning of the radiation therapy is done e.g. by using computer tomography images. These images are nowadays more and more frequently combined with images from other image generating devices such as magnetic camera images (a magnetic camera is normally referred to as MRI=magnetic resonance imaging) and images from a PET camera (PET=Positron Emission Tomography) in order to determine the extension of tumour in three dimensions, and also to determine the nature of the tumour.

In order to minimize the side effects on normal healthy tissue repeatedly radiation doses normally are given. During the imaging procedures it is important to carefully reposition the body and the tumour area according to predetermined parameters so the tumour area not will be missed.

Electronic image giving plates have been used for many years in order to control the position of the skeleton when using high energetic therapy beams on 4-20 megavolts (MV), which normally are used. In recent years the beam accelerators that give rise to the radiation doses have been equipped with complementary equipment resulting in x-ray beams in the kilovolt area (kV). These beams in the kV area have properties differentiated from the high energetic MV beam. The beams in the kV area are decelerated not only by the mass coming in its way, but also by a decelerating force in relation to the density of the material that the beams are passing by and the decelerating force is increasing almost exponentially with higher density.

Positioning markers are used in order to show the location of a tumour in a human or an animal tissue in order to accurately be able to identify the tumour when repeated images are obtained, and in particular when various imaging devices are used. These markers are decelerating the x-ray beams so much that the marker becomes visible on monitors where the results from different media are shown. Gold has a high density of 19.3 g/cm$^3$, which makes it advantageously to be used as decelerating substance for the beams. Pure gold is also soft and possible to shape and is tolerated by the body as it is an inert material. The volume of gold may be limited so the substance becomes a thin wire, which also means that the marker may be inserted into the body by means of thin needles. Thereby the risk of bleedings and infections is minimized. Such a marker of gold is known by e.g. U.S. Pat. No. 8,406,054, which also is incorporated herein in its entirety.

Markers that are put into tissue of human or animal will rest mainly in the same place the entire life. Thus, it is extremely important that the markers not cause mechanical damage or give rise to allergies or other state of ill-health. The marker must have sufficient size and have an appropriate density in order for the marker to be clearly depicted at MR examination. The marker is an elongated object with a longitudinal axis and with a diameter of at the most 0.50 mm, e.g. 0.28 mm. The marker further has a predetermined total length, in the range of 5-30 mm, e.g. 10 mm or 20 mm. The marker comprises a plurality of first segments and a plurality of second segments, wherein the first and second segments are arranged alternately after each other. In one variation the marker comprises a first material, e.g. gold, with a density of at least 10 g/cm$^3$, and this material constitute at least 90% by volume of the marker, and a second material, a ferromagnetic material, that is magnetic and that constitute at the most 10% by volume of the marker.

The positioning marker is inserted into tissue by an insertion needle, being a part of a medical insertion device, which is provided with an insertion needle having a distal end where the positioning marker is located prior insertion into the tissue.

When preparing the implantation of the marker it must be transferred from a loader needle provided with the marker to the distal end of the insertion needle. In some cases, not applicable when using a marker loading assembly disclosed herein, the marker may be inserted directly through the skin without transferring it to an insertion needle of a medical insertion device. The object of the marker loading assembly is to facilitate accurate and user-friendly transferring of the positioning marker to the insertion needle.

SUMMARY

The present invention provides a marker loading assembly for transferring an elongated positioning marker from a loader needle of the assembly into an insertion needle of a medical insertion device.

The marker loading assembly comprises
  an elongated hollow housing having a manoeuvring end and a marker transfer end, and
  a loader needle mounted within the loading assembly along a longitudinal axis of the assembly, the loader needle being adapted to receive and hold the positioning marker until the positioning marker is transferred to said insertion needle,
  a transfer opening provided at the marker transfer end and being adapted to receive a distal end of the insertion needle, said transfer opening being provided with a shape gradually opening up in a direction away from said manoeuvring end, and said transfer opening at its narrow end leading to a transfer channel arranged along said longitudinal axis.

The transfer channel has a circular cross-sectional shape having a diameter slightly larger than an outer diameter of the insertion needle or of an outer protective sleeve provided on the outside of the insertion needle.

A loading end of the loader needle is concentrically arranged in the transfer channel such that an annular space having a predetermined length along the longitudinal axis is provided around the loading end.

The outer diameter of the loader needle is slightly smaller than the inner diameter of the insertion needle, which enables the distal end of the insertion needle to be inserted into said annular space in the transfer channel and simultaneously the loading end of the loader needle to be inserted into the distal end of the insertion needle to set said assembly in a marker loading ready state.

The loading assembly further comprises a transfer mandrel, the transfer mandrel being adapted to be arranged within the loading needle and being arranged to receive a force in the direction towards the insertion needle and thereby achieve transfer of the marker from the loader needle into the distal end of the insertion needle.

DETAILED DESCRIPTION

The marker loading assembly will now be described in detail with references to the appended figures. Throughout the figures the same, or similar, items have the same reference signs. Moreover, the items and the figures are not necessarily to scale, emphasis instead being placed upon illustrating the principles of the invention.

Figure 1:
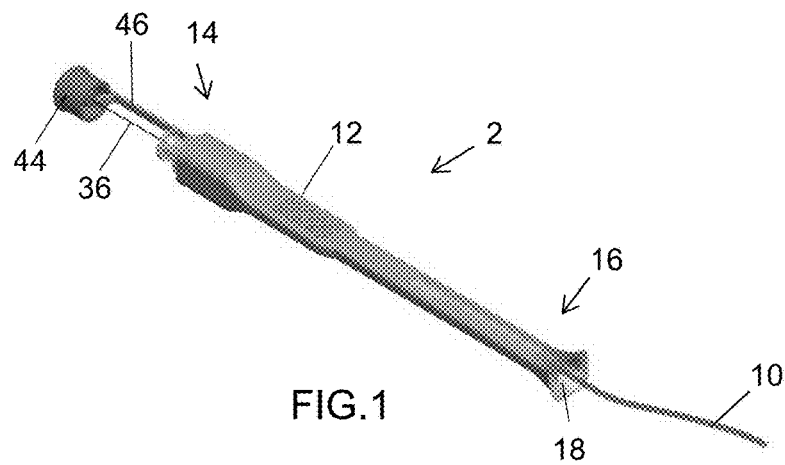
FIG. 1 is a perspective image of the marker loader assembly.

In FIG. 1 a perspective view of the marker loading assembly 2 is shown. The various details indicated in that figure will be discussed in detail with references to the other figures.

Figure 3:
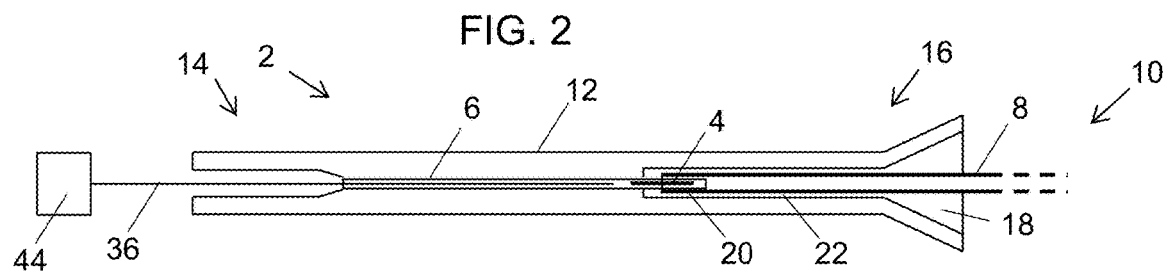
Figure 7:
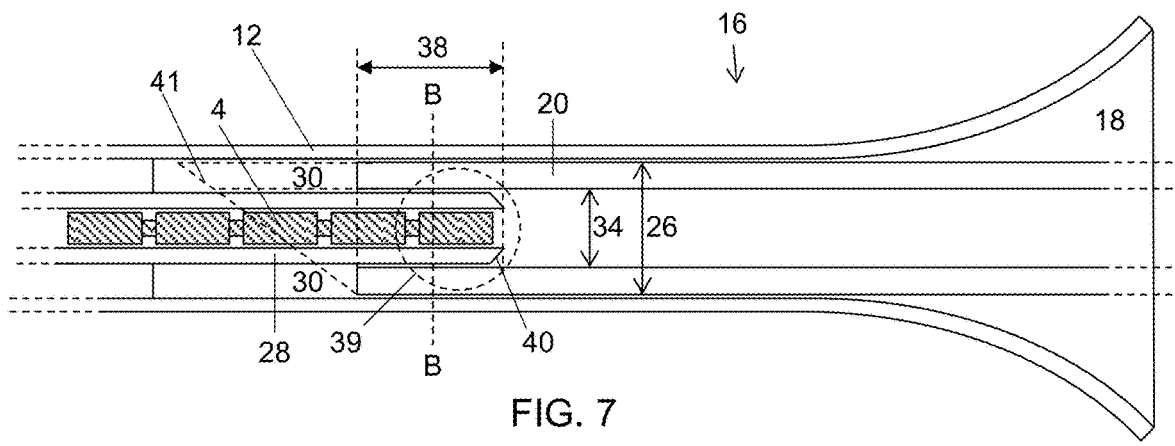

We now refer in particular to FIGS. 3 and 7 where a marker loading assembly 2, is disclosed, for transferring an elongated positioning marker 4 from a loader needle 6 of the assembly into an insertion needle 8 of a medical insertion device 10. The insertion needle may be provided with a protective sleeve concentrically arranged outside the insertion needle. The sleeve is not shown in the figures. The medical insertion device including the insertion needle, and also the protective sleeve if present, is in its turn configured to be inserted into the human or animal body via an insertion channel in a bronchoscope, gastroscope, colonoscope or similar equipment conventionally used for in-vivo diagnostics, therapy, etc.

In one advantageous application the medical insertion device is an endoscopic ultrasound aspiration needle.

Figure 6:
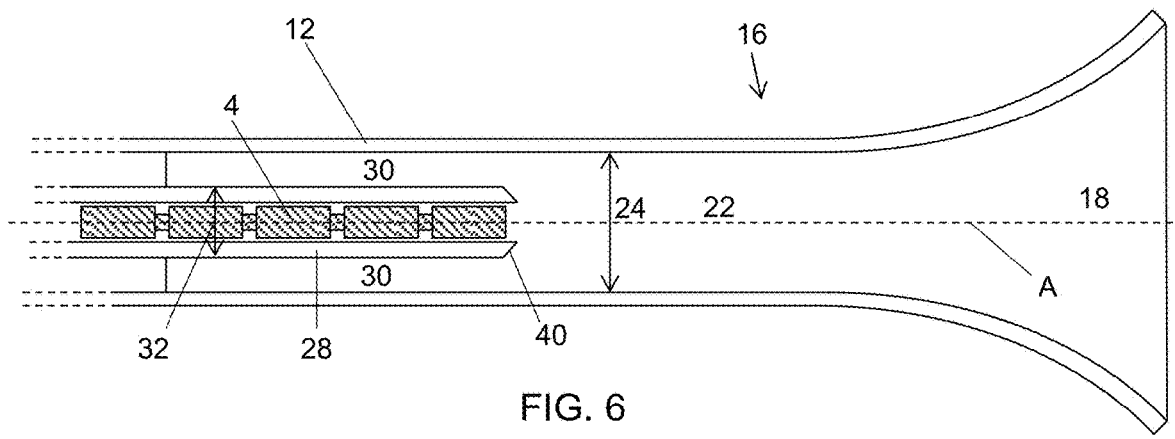
FIGS. 6-8 are schematic cross-sectional views of various states of the marker transfer end of the marker loader assembly.
Figure 8:
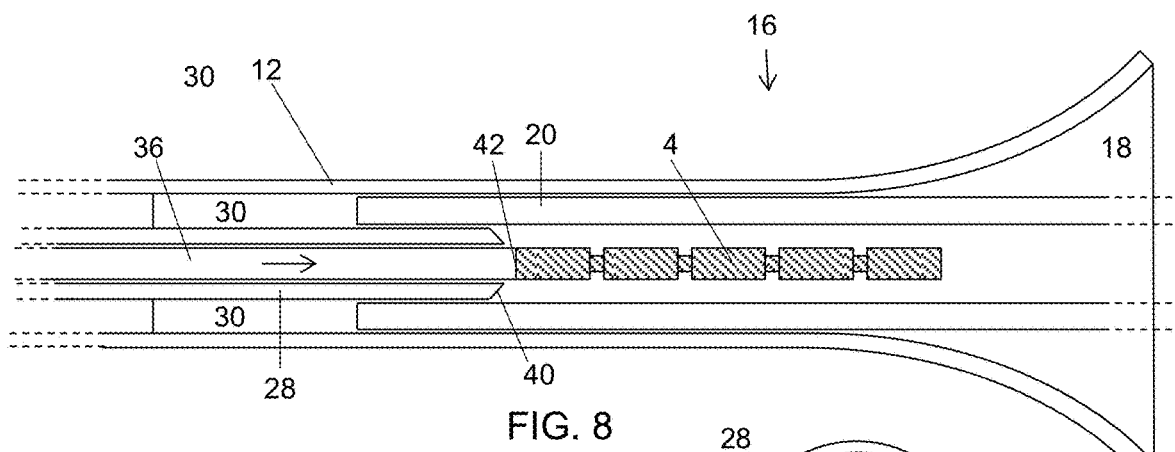

The positioning marker is preferably of the kind disclosed in the above-mentioned US-2014/0088419. In FIGS. 6-8 the marker is provided with indentations which may be regularly or irregularly distributed along the marker. The indentations are essential in order for the marker to fold in a controlled manner when inserted into tissue.

The marker loading assembly comprises an elongated hollow housing 12 having a manoeuvring end 14 and a marker transfer end 16, and a loader needle 6 mounted within said loading assembly 2 along a longitudinal axis A of the assembly. The loader needle being adapted to receive and hold the positioning marker until the positioning marker is transferred to said insertion needle. The loader needle is e.g. 50-100 mm long, in one embodiment about 70 mm.

Furthermore, a transfer opening 18 provided at the marker transfer end and being adapted to receive a distal end 20 of the insertion needle 8. The transfer opening 18 being provided with a shape gradually opening up in a direction away from the manoeuvring end 14, and the transfer opening 18 at its narrow end leading to a transfer channel 22 arranged along the longitudinal axis A.

The transfer channel 22 has a circular cross-sectional shape having a diameter 24 slightly larger than an outer diameter 26 of the insertion needle 8 or of an outer protective sleeve provided on the outside of the insertion needle 8. Preferably, the transfer channel 22 has a diameter in the range of 0.5-2.0 mm.

A loading end 28 of the loader needle 6 is concentrically arranged in the transfer channel 22 such that an annular space 30 having a predetermined length L along the longitudinal axis A is provided around the loading end 28.

The outer diameter 32 of the loader needle 6 is slightly smaller than the inner diameter 34 of the insertion needle 8. Preferably, the loader needle has an outer diameter in the range of 0.4-0.8 mm. This enables the distal end of the insertion needle to be inserted into the annular space 30 in the transfer channel 22 and simultaneously the loading end 28 of the loader needle 6 to be inserted into the distal end 20 of the insertion needle 8 to set the assembly in a marker loading ready state. This state is illustrated in FIGS. 3 and 7.

The marker loading assembly further comprises a transfer mandrel 36 which is illustrated in FIGS. 1-5, and 8. The transfer mandrel 36 being adapted to be arranged within the loader needle 6 and being arranged to receive a force in the direction towards the insertion needle 8 and thereby achieve transfer of the marker 4 from the loading needle 6 into the distal end 20 of the insertion needle 8. When the assembly is in a marker loading ready state an overlap 38 (see FIGS. 3 and 7) is provided along the longitudinal axis A between the most foremost ends of the loading end 28 and of the distal end 20 of the insertion needle.

To ensure that the marker loading assembling is in its ready state a transparent inspection window 39, or an inspection hole 39, is provided in the housing such that a user easily may ascertain that the insertion needle is in a correct positon for transferring the marker. The window, or the hole, 39 is schematically indicated by a dashed circle in FIG. 7 but may have any appropriate shape (rectangular, elliptical, etc.), and may be arranged at any position along the transfer channel.

Advantageously, the most foremost end 40 of the loading end 20 of the loader needle 6 is cut in a direction essentially perpendicular to the longitudinal axis A of the needle, and is chamfered outwardly in order to further facilitate that the distal end 20 of the insertion needle 8 is guided such that the loading end 20 of the loader needle 6 is inserted into the insertion needle. The foremost end of the distal end 20 is e.g. cut off essentially in a perpendicular direction in relation to axis A, but may also have an oblique needle tip 41 which is indicated by dashed lines in FIG. 7.

The shape of the transfer opening 18 is such that the distal end 20 of the insertion needle 8 easily may be guided into the transfer channel 22, and the transfer opening has therefore a width being large enough to ensure that an operator safely may insert the distal end. The width may be in the range of approximately 5-20 mm, and most preferred in the range of 8-12 mm. Preferably, the transfer opening essentially has a shape of a funnel in the direction away from said manoeuvring end, but other shapes are naturally also possible, e.g. an essentially rectangular shape as illustrated in FIG. 1 having rounded corners.

The marker loading assembly preferably comprises a lubricating material, e.g. medical unrestricted silicone, which is pre-applied to the positioning marker. The lubricating material will facilitate easy transfer of the marker to the medical insertion device, and also facilitate the eventual insertion of the marker from the insertion device into the body. In addition the lubricating material will make the marker stick to the inner walls of the loader needle which is advantageous e.g. during transportation of the loading assembly.

The transfer mandrel 36 has a longitudinal extension having a shape of a solid rod having a blunt distal end 42 with a cut-off surface essentially perpendicular to the longitudinal axis of the mandrel 36. The mandrel has an outer diameter slightly less than the inner diameter of the loader needle 6, such that it easily may be inserted into, and moved within the loader needle 6. The proximal end 44 of the transfer mandrel is provided with an operating member, e.g. in the shape of a knob, or handle, for an operator when performing the transferring action.

The transfer mandrel is movable between a proximal position and a distal position. In the proximal position the distal end is within the loader needle at a position such that a required longitudinal space within the loader needle is left for the marker to be arranged in the loading end of the loader needle. Preferably, a holder member 46 is provided structured to hold the transfer mandrel in its proximal position, and in particular cooperate with the operating member, e.g. during transportation of the assembly, such that the transfer mandrel is prevented from moving in the distal direction. The holder member is shown in FIG. 1. When transfer of the marker is about to take place the operating member may easily be released from the holder member.

The use of the marker loading assembly will now be described by in particular referring to FIGS. 2-4 that show successive states during the procedure of transferring the marker to the insertion needle. FIGS. 6-8 illustrate the respective successive states of the marker transfer end 16 in a larger scale. In FIG. 5 the insertion needle is withdrawn from the assembly.

Figure 2:
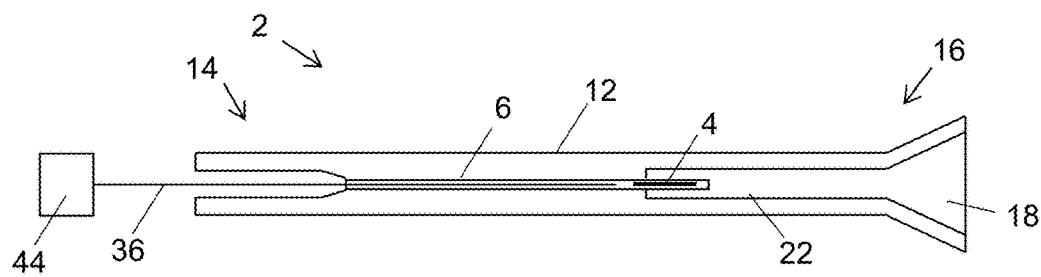
FIGS. 2-5 are schematic cross-sectional views of various states of the marker loader assembly.

Thus, in FIG. 2 is shown the marker loading assembly in a marker loading state.

Figure 4:
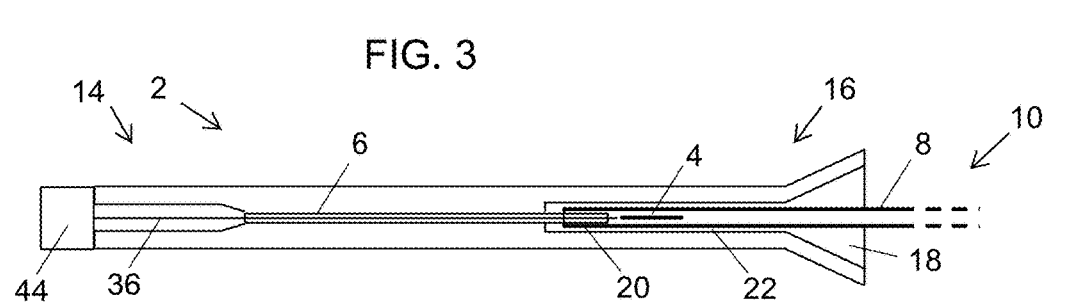
Figure 5:
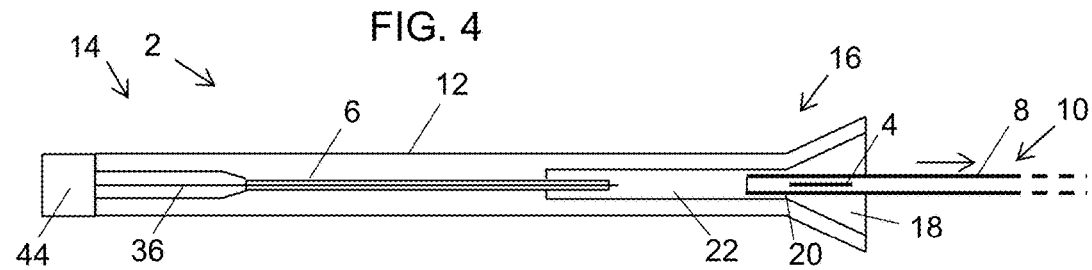

Transfer of the marker is achieved by moving/pushing the transfer mandrel 36 in the distal direction to the distal position and a blunt distal end 42 will then push the marker into the insertion needle—see FIGS. 4 and 8 where it is illustrated the state when the marker has been transferred into the insertion needle. The mandrel has a predefined length such that in its distal position the blunt distal end of the transfer mandrel is just beyond the foremost end of the loading end of the loader needle.

Figure 9:
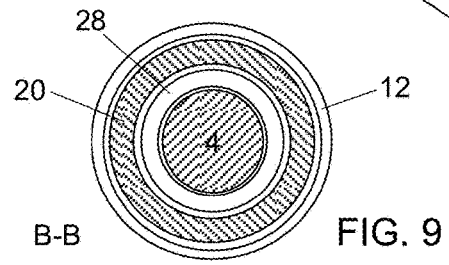
FIG. 9 is a cross-sectional view along B-B in FIG. 7.

FIG. 9 is cross-sectional view along B-B in FIG. 7, when the assembly is in the marker transfer state where the marker 4 is within the loading end 28 of the loader needle and is about to be transferred the insertion needle 8.

Furthermore, the marker loading assembly is preferably made from a transparent material, e.g. plastic, and may be injection moulded in two halves to be mounted together.

In still another variation, the assembly comprises a removable transport protecting member being an essentially elongated rod structured to be inserted into the loading end of the loader needle, and having a shape that via friction holds the protecting member within the needle, e.g. during transportation. The transport protecting member easily is removed from the loader needle when the assembly is to be used.

The present invention is not limited to the above-described preferred embodiments. Various alternatives, modifications and equivalents may be used. Therefore, the above embodiments should not be taken as limiting the scope of the invention, which is defined by the appending claims.

What is claimed is:

1. An imaging marker loading assembly for transferring an elongated positioning marker from a loader needle of said assembly into an insertion needle of a medical insertion device, the marker loading assembly comprising:
   an elongated hollow housing having a manoeuvring end and a marker transfer end,
   a loader needle mounted within said loading assembly along a longitudinal axis of said assembly, said loader needle supporting therein said elongated positioning marker until the elongated positioning marker is transferred to said insertion needle, said elongated positioning marker having one or more indentations distributed along a longitudinal axis of said elongated positioning marker for enabling the elongated positioning marker to fold when inserted into tissue, wherein the elongated positioning marker is configured to form an entangled ball when inserted into tissue, and
   a transfer opening provided at the marker transfer end and being adapted to receive a distal end of the insertion needle, said transfer opening being provided with a shape gradually opening up in a direction away from said manoeuvring end, and said transfer opening at its narrow end leading to a transfer channel arranged along said longitudinal axis,
   a removable transport protecting member being an elongated rod structured to be inserted into a loading end of the loader needle, frictionally held within the loader needle, and easily removed from the loader needle when the assembly is to be used,
   wherein the transfer channel has a circular cross-sectional shape having a diameter larger than an outer diameter of the insertion needle or of an outer protective sleeve provided on the outside of the insertion needle, and wherein a loading end of the loader needle is concentrically arranged in the transfer channel such that an annular space having a predetermined length along the longitudinal axis is provided around the loading end,
   wherein the outer diameter of the loader needle is smaller than an inner diameter of the insertion needle, which enables the distal end of the insertion needle to be inserted into said annular space in the transfer channel and simultaneously the loading end of the loader needle to be inserted into the distal end of the insertion needle to set said assembly in a marker loading ready state, and
   wherein the loading assembly further comprises a transfer mandrel, said transfer mandrel being adapted to be arranged within said loading needle and being arranged to receive a force in the direction towards the insertion needle and thereby achieve transfer of the elongated positioning marker from the loader needle into the distal end of the insertion needle.

2. The imaging marker loading assembly according to claim 1, wherein said transfer opening has a shape of a funnel in the direction away from said manoeuvring end.

3. The imaging marker loading assembly according to claim 1, in combination with the insertion needle in a marker loading ready state wherein an overlap is provided along the longitudinal axis between the most foremost ends of the loading end and of the distal end of the insertion needle.

4. The imaging marker loading assembly according to claim 1, wherein said transfer channel has a diameter in the range of 0.5-2.0 mm.

5. The imaging marker loading assembly according to claim 1, wherein said loader needle has an outer diameter in the range of 0.4-0.8 mm.

6. The imaging marker loading assembly according to claim 1, wherein said transfer mandrel has a longitudinal extension having a shape of a solid rod having a blunt distal end with a cut-off surface perpendicular to the longitudinal axis of the mandrel, and that the mandrel has an outer diameter less than the inner diameter of the loader needle, such that it easily may be inserted into, and moved within the loader needle.

7. The imaging marker loading assembly according to claim 6, wherein the proximal end of the transfer mandrel is provided with an operating member having the shape of a knob, or handle, for an operator when performing the transferring action.

8. The imaging marker loading assembly according to claim 1, wherein said transfer mandrel is movable between a proximal position and a distal position, in the proximal position the distal end is within the loader needle at a position providing a longitudinal space within the loader needle in which is fully contained the elongated positioning marker.

9. The imaging marker loading assembly according to claim 8, configured such that transfer of the marker is achieved by moving or pushing the transfer mandrel in the distal direction to the distal position and a blunt distal end will then push the elongated positioning marker into the insertion needle, and that the mandrel has a predefined length such that in its distal position the blunt distal end of the transfer mandrel is beyond the distal end of the loader needle.

10. The imaging marker loading assembly according to claim 1, wherein said assembly comprises a lubricating material that is applied to the elongated positioning marker.

11. The imaging marker loading assembly according to claim 1, wherein the most foremost end of the loading end of the loader needle is cut in a direction perpendicular to the longitudinal axis of the needle, and is chamfered outwardly in order to further facilitate that the distal end of the insertion needle is guided such that the loading end of the loader needle is inserted into the insertion needle.

12. The imaging marker loading assembly according to claim 1, wherein the marker loading assembly is made from a transparent material and may be injection moulded in two halves to be mounted together.

13. An imaging marker loading assembly for transferring an elongated positioning marker from a loader needle of said assembly into an insertion needle of a medical insertion device, the marker loading assembly comprising:
 an elongated hollow housing having a manoeuvring end and a marker transfer end,
 a loader needle mounted within said loading assembly along a longitudinal axis of said assembly, said loader needle being adapted to receive and hold said positioning marker until the elongated positioning marker is transferred to said insertion needle,
 a transfer opening provided at the marker transfer end and being adapted to receive a distal end of the insertion needle, said transfer opening being provided with a shape gradually opening up in a direction away from said manoeuvring end, and said transfer opening at its narrow end leading to a transfer channel arranged along said longitudinal axis, and
 a removable transport protecting member being an elongated rod structured to be inserted into a loading end of the loader needle, frictionally held within the loader needle, easily removed from the loader needle when the assembly is to be used,
wherein the transfer channel has a circular cross-sectional shape having a diameter larger than an outer diameter of the insertion needle or of an outer protective sleeve provided on the outside of the insertion needle, and wherein a loading end of the loader needle is concentrically arranged in the transfer channel such that an annular space having a predetermined length along the longitudinal axis is provided around the loading end,
wherein the outer diameter of the loader needle is smaller than an inner diameter of the insertion needle, which enables the distal end of the insertion needle to be inserted into said annular space in the transfer channel and simultaneously the loading end of the loader needle to be inserted into the distal end of the insertion needle to set said assembly in a marker loading ready state, and
wherein the loading assembly further comprises a transfer mandrel, said transfer mandrel being adapted to be arranged within said loading needle and being arranged to receive a force in the direction towards the insertion needle and thereby achieve transfer of the elongated positioning marker from the loader needle into the distal end of the insertion needle.

* * * * *